United States Patent

Löffler et al.

(10) Patent No.: US 6,437,068 B2
(45) Date of Patent: Aug. 20, 2002

(54) WATER-SOLUBLE OR WATER-SWELLABLE CROSSLINKED COPOLYMERS

(75) Inventors: Matthias Löffler, Niedernhausen; Roman Morschhäuser, Mainz, both of (DE)

(73) Assignee: Clariant GmbH, Frankfurt (DE)

( * ) Notice: Subject to any disclaimer, the term of this patent is extended or adjusted under 35 U.S.C. 154(b) by 11 days.

(21) Appl. No.: 09/760,317

(22) Filed: Jan. 11, 2001

(30) Foreign Application Priority Data

Jan. 11, 2000 (DE) .......................... 100 00 648

(51) Int. Cl.⁷ .............................. C08F 226/06

(52) U.S. Cl. ................................... 526/264

(58) Field of Search ........................ 526/264

(56) References Cited

U.S. PATENT DOCUMENTS

| | | | |
|---|---|---|---|
| 4,619,773 A | 10/1986 | Heilweil et al. |
| 5,080,809 A | 1/1992 | Stahl et al. |
| 5,510,436 A | 4/1996 | Hille et al. |
| 6,120,780 A | 9/2000 | Dupuis et al. |

FOREIGN PATENT DOCUMENTS

| | | |
|---|---|---|
| CA | 2209060 | 12/1997 |
| DE | 199 05 639 | 8/2000 |
| EP | 0 483 638 | 5/1992 |
| EP | 0 510 246 | 10/1992 |
| EP | 0 815 828 | 1/1998 |
| EP | 0 816 403 | 1/1998 |
| WO | WO 98/00094 | 1/1998 |

OTHER PUBLICATIONS

EPO Search Report For Application No. EP 00710047; Dated May 21, 2001.

Kosmetische Farbemittel [Cosmetic Colorants] from the Farbstoffkommission der Deutschen Forschungsgemeinschaft [Dyes Commission of the German Research Society], Verlag Chemie, Weinheim, pp. 81–106, 1984.

U.S. application No. 09/501,904.

Primary Examiner—Christopher Henderson
(74) Attorney, Agent, or Firm—Richard P. Silverman

(57) ABSTRACT

Water-soluble or water-swellable crosslinked copolymers consisting essentially of structural units of the formula 1

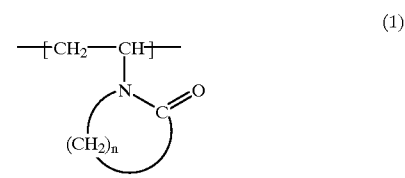

(1)

or a mixture of the structural units of the formula 1 with structural units of the formula 2

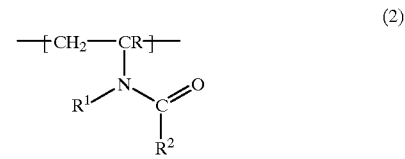

(2)

and structural units of the formula 3

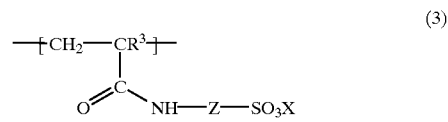

(3)

where R, $R^1$, $R^2$, $R^3$, Z and n are as defined in the description. These copolymers are crosslinked with compounds which contain at least two olefinic double bonds. These crosslinked copolymers are suitable as thickeners, in particular for cosmetic and pharmaceutical preparations.

4 Claims, No Drawings

WATER-SOLUBLE OR WATER-SWELLABLE CROSSLINKED COPOLYMERS

FIELD OF THE INVENTION

The present invention relates to water-soluble or water-swellable crosslinkable copolymers based on ammonium salts of acrylamidoalkylsulfonic acids and cyclic N-vinylcarboxamides or cyclic and linear N-vinylcarboxamides, to the preparation thereof and to the use thereof as thickeners, stabilizers of emulsions and dispersions and as glidants in cosmetic and pharmaceutical compositions.

BACKGROUND OF THE INVENTION

Water- or solvent-containing multicomponent systems, such as solutions, emulsions or suspensions, are frequently adjusted to higher viscosities or thickened for economical or performance reasons, or for stability reasons. Thus, for example, by increasing the viscosity of the external or internal phase of emulsions or suspensions, it is possible to significantly prolong the time before the components of such a system separate, which is evident from an extension of the shelf life. For many products, increasing the viscosity also improves their ability to be spread uniformly, in particular on uneven surfaces. This is true in particular for skincare compositions and pharmaceutical ointments on the skin. In the case of many industrial products, such as wallpaper stripping agents, paint strippers or aircraft de-icers, the increased viscosity prevents premature run-off from the surface to be treated. The more uniform distribution and extended contact time thus increase the effectiveness. As well as the performance advantages mentioned, the high viscosity of such preparations also offers further advantages during the preparation, packaging, containerizing and storage, as well as during transportation, the thickening of acidic media being of particular importance here from a safety viewpoint. In general, the rheological properties during the preparation and/or formulation of cosmetic, pharmaceutical or industrial preparations are a decisive criterion for the use of these products in practice. Even when used in extremely small amounts, the thickeners employed should lead to adequate thickening. However, the color and principal properties of the medium to be thickened should not be changed.

To adjust the rheological properties of aqueous or solvent-containing systems, emulsions, suspensions, a large number of different systems are given in the specialist literature. Known examples are cellulose ethers and other cellulose derivatives (e.g. carboxymethylcellulose, hydroxyethylcellulose), gelatin, starch and starch derivatives, sodium alginates, fatty acid polyethylene glycol esters, agar agar, tragacanth or dextrins. The synthetic polymers used are various materials, such as e.g. polyvinyl alcohols, polyacrylamides, polyacrylic acid and various salts of polyacrylic acid, polyvinylpyrrolidone, polyvinyl methyl ether, polyethylene oxides, copolymers of maleic anhydride and vinyl methyl ether, and various mixtures and copolymers of the compounds given above.

However, said compounds exhibit diverse disadvantages upon use. Thus, for example, the cellulose derivatives and, generally, the materials based on natural raw materials and the formulations resulting therefrom are very susceptible to bacteria. From an applications-related viewpoint, they are mostly noticeable from the formation of unpleasant "stringing" gels. Fatty acid polyethylene glycol esters tend toward hydrolysis in the presence of water, and the insoluble fatty acids which form in the process cause undesired clouding. Thickeners of natural origin (e.g. agar agar or tragacanth) have a composition which varies considerably depending on their origin.

EP-A-0 816 403 and WO 98/00094 describe crosslinked homopolymers of 2-acrylamido-2-methylpropanesulfonates and the use thereof as thickeners. EP-A-0 510 246 describes crosslinked copolymers of N-vinylcarboxamides and unsaturated alkylamides substituted by a sulfonate group, which are likewise suitable as thickeners. U.S. Pat. No. 5,080,809 describes non-crosslinked copolymers of N-vinylpyrrolidone and 2-acrylamido-2-methylpropanesulfonate. DE 199 05 639.0 describes crosslinked polymers of noncyclic N-vinylcarboxamides and acrylamidoalkylsulfonic acids.

SUMMARY OF THE INVENTION

Surprisingly, we have now found that alkali metal, alkaline earth metal or ammonium salts of various acrylamidoalkylsulfonic acids are sufficiently soluble in solvents acceptable for cosmetic applications, such as alcohols or alcohol mixtures, and are therefore highly suitable for a copolymerization with cyclic N-vinylcarboxamides which are likewise soluble in these solvents, or mixtures of two or more cyclic N-vinylcarboxamides or mixtures of cyclic and linear N-vinylcarboxamides, optionally with further monomers, and monomers which act as crosslinkers. In contrast to this, according to the prior art, it is obligatory to work in an aprotic solvent. Since the ammonium salt of 2-acrylamido-2-methylpropanesulfonic acid, which is preferably used for the polymerization, is in ionic form the crosslinked copolymer obtained no longer needs to be subsequently neutralized in an involved manner, but can be used as a thickener immediately following polymerization and removal of the solvent. A further advantage is that through appropriate choice of the comonomer(s) (cyclic N-vinylcarboxamides, mixtures of cyclic and linear N-vinylcarboxamides) it is possible to control the ratio of ionic to neutral building blocks and thus to regulate the thickening action and salt stability and better match them to specific requirements. Furthermore, as result of the polymerization in alcohol or alcohol mixtures with a water content of less than 10% by weight and here in particular in tert-butanol, products are obtained which, with regard to their residual content of solvent remaining in the product, are toxicologically safe and can thus be used, for example, in cosmetic products.

The invention provides crosslinked copolymers consisting essentially of a1) 1 to 50% by weight of the repeating structural unit of the formula (1)

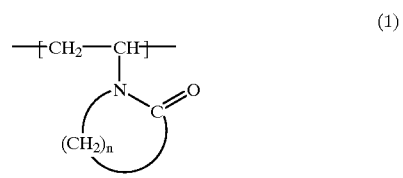

where n is an integer from 2 to 9, or a2) 1 to 50% by weight of a mixture of the repeating structural unit of the formula (1) and of the repeating structural unit of the formula (2)

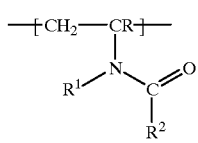

where R, R$^1$ and R$^2$ may be identical or different and are hydrogen or a linear or branched alkyl or alkenyl group having in each case 1 to 30, preferably 1 to 20, in particular 1 to 12, carbon atoms and b) 49.99 to 98.99% by weight of the repeating structural unit of the formula (3)

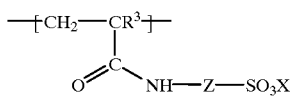

in which R$^3$ is hydrogen, methyl or ethyl, Z is $C_1$–$C_8$-alkylene, n is an integer from 2 to 9, and X is an alkali metal or alkaline earth metal ion, and c) 0.01 to 8% by weight, preferably 0.01 to 5% by weight, of crosslinking structures resulting from monomers having at least two olefinic double bonds.

Preferred copolymers according to the invention contain 2 to 30% by weight, in particular 3 to 15% by weight, of structural units of the formula (1), or (1) and (2), preferably derived from N-vinylpyrrolidone, 69.5 to 97.5% by weight, in particular 84.5 to 96.5% by weight, of structural units of the formula (3), preferably derived from the ammonium salt of 2-acrylamido-2-methylpropanesulfonic acid and 0.2 to 3% by weight, in particular 0.5 to 2% by weight, of crosslinking structures resulting from monomers having at least two olefinic double bonds. The mixing ratio of the monomers forming the basis of structural units 1 and 2 can be varied within any desired limits.

Crosslinking structures resulting from monomers having at least two olefinic double bonds are preferably derived from allyl acrylate or allyl methacrylate, dipropylene glycol diallyl ether, polyglycol diallyl ether, triethylene glycol divinyl ether, hydroquinone diallyl ether, tetraallyloxyethane or other allyl or vinyl ethers of multifunctional alcohols, tetraethylene glycol diacrylate, triallylamine, trimethylolpropane diallyl ether, methylene bisacrylamide or divinylbenzene. The crosslinking structures are particularly preferably derived from monomers of the formula (4),

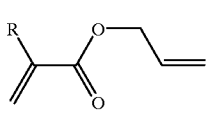

in which R is hydrogen, methyl or ethyl.

The copolymers according to the invention are prepared by dissolving or dispersing the monomers corresponding to the repeating structural units of the formulae (1), (2) and (3) in a protic solvent, adding one or more crosslinkers having at least two olefinic double bonds to this solution or dispersion, and starting the polymerization in a manner known per se by adding a free-radical- forming compound.

Preference is given to copolymerizing the ammonium salt of acrylamidopropanesulfonic acid. Instead of this ammonium salt, it is also possible to use the free acrylamidopropanesulfonic acid and, before adding the remaining monomers, producing the ammonium salt from the free acid by introducing ammonia.

The polymerization reaction is preferably carried out in a water-soluble alcohol or a mixture of two or more alcohols having 1 to 6 carbon atoms, preferably in tert-butanol. The water content of the alcohol or of the mixture of two or more alcohols must not exceed 10% by weight since otherwise the formation of lumps can occur over the course of the polymerization. Specifically, the type and amount of solvent are chosen such that the salt of acrylamidoalkylsulfonic acid of the formula 1, in particular of 2-acrylamido-2-methylpropanesulfonic acid, is largely soluble or dispersible therein. Largely soluble or dispersible is understood as meaning that even after the stirrer has been switched off, no solid material settles out of the solution or dispersion. By contrast, the polymer formed in the course of the reaction should be largely insoluble in the chosen solvent (or solvent mixture). Largely insoluble is understood here as meaning that in the course of the polymerization a readily stirrable pulpy polymer paste is produced in which no lumps or agglutinations must form. The filtrate which is obtainable by filtering the paste with suction must have a solids content of at most 5% by weight. If the copolymers are soluble in the chosen solvent or solvent mixture to a greater extent, clumping may result during drying of the polymer paste. The polymerization reaction itself is triggered in a manner known per se by free-radical-forming compounds, such as azo initiators (e.g. azobisisobutyronitrile), peroxides (e.g. dilauryl peroxide) or persulfates in a suitable temperature range from 20 to 120° C., preferably between 40 and 80° C., and is continued over a period of from 30 min to several hours.

The copolymer composition can be varied by varying the above-described ratio of the monomers used, and the proportion of crosslinker and thus be used to achieve a tailored profile of properties. For example, by incorporating more ammonium salts of acrylamidosulfonic acids, it is possible to improve the thickening action of the polymers, while by incorporating more cyclic N-vinylcarboxamide, it is possible to improve the electrolyte compatibility of the polymers and the solubility thereof in nonaqueous systems. In contrast to polymers based on acrylic acid which, in the neutral or slightly alkaline range in 1% strength aqueous solution, exhibit viscosities of more than 30 000 mPa.s, but whose thickening ability (or the measured viscosity) deteriorates considerably with decreasing pH, the copolymers described according to the invention are able to maintain their viscosity up to an acidic pH of about 3.

EXAMPLES

Example 1

A 1000 ml flask fitted with anchor stirrer, reflux condenser, internal thermometer, feed option for $N_2$ and $NH_3$ was charged with 490.5 g of tert-butanol and 11.5 g of water. 80.75 g of 2-acrylamido-2-methylpropanesulfonic acid were then introduced and dispersed with vigorous stirring, clouding of the solvent being retained. Over a period of 30 min, 6.64 g of ammonia were introduced into the overhead gas space and the mixture was stirred for at least a further 30 min until a pH of 6–7 had been established. 4.10 g of N-vinylpyrrolidone and 0.8 g of allyl methacrylate were added, and the receiver was rinsed in each case with tert-butanol (about 6 ml) in order to minimize losses during the addition. The reaction mixture was then heated to a temperature of T=60° C., the reaction mixture being rendered inert by the simultaneous introduction of $N_2$. After the temperature of T=60° C. had been reached, 1.0 g of dilauryl peroxide was added. The reaction started immediately after the initiator had been added, being recognizable from an increase in the temperature and from flocculation of the polymer. Approximately 15 minutes after the polymerization reaction had started, the nitrogen feed was switched off. Approximately 30 minutes after the initiator dilauryl peroxide had been added, the temperature reached a maximum (about 65–70° C.). For a further 30 minutes after this maximum had been passed, the mixture was heated to reflux and then stirred under these conditions for two hours. The contents of the reaction vessel developed a pulp-like consistency over the course of the reaction, but was still readily stirrable. The mixture was then cooled to room temperature and the solid was filtered off with suction. The paste was dried at 60–70° C. in a vacuum drying cabinet for 24 hours, giving 92.2 g of a fine white powder.

Example 2

Example 1 was repeated except that instead of allyl methacrylate as crosslinker, 1.65 g of trimethylolpropane methacrylate were used.

Example 3

In accordance with Example 1, the crosslinked copolymer was prepared from 35 g of 2-acrylamido-2-methylpropanesulfonic acid, 55 g of N-vinylpyrrolidone and 1.9 g of trimethylolpropane triacrylate.

Example 4

In accordance with Example 1, the crosslinked copolymer was prepared from 77.5 g of 2-acrylamido-2-methylpropanesulfonic acid, 8.9 g of N-vinylpyrrolidone, 4.2 g of N-vinylformamide and 1.8 g of trimethylolpropane triacrylate.

Comparative Example 1

In accordance with Example 1, a crosslinked homopolymer was prepared from 85 g of 2-acrylamido-2-methylpropanesulfonic acid and 0.8 g of allyl methacrylate.

Test Results:

The powders obtained according to the examples were in each case dissolved in an amount of 1.0% by weight in distilled water, and the viscosity of the gels thereby formed was measured at 25° C. For this, 5 g of dried polymer powder were in each case stirred into 495 g of distilled water in a 600 ml beaker, and the viscosity of the gel thereby formed was measured using a Brookfield RVT type viscometer at 20 rpm. The gels prepared in this way are particularly suitable for cosmetic applications since they impart a pleasant feel to the skin when spread on the body.

The acid stability was likewise determined by measuring the viscosity using the Brookfield viscometer. For this, the copolymer prepared as in Preparation Example 1 was compared with a commercially available polymer based on acrylic acid (Carbopol® 934 from Goodrich). 1.0% strength gels of both polymers were prepared according to the method described above, their pH being adjusted, where appropriate to an acidic value (pH=about 3) and to a neutral value (pH=6–7) by adding NaOH and $H_3PO_4$, respectively.

TABLE

Measured viscosities of the 1.0% strength gels

| pH | Polymer from Example 1 | Carbopol 934 |
|---|---|---|
| 6–7 | 65 600 mPa · s | 76 600 mPa · s |
| about 3 | 52 100 mPa · s | 140 mPa · s |

As the table shows, in contrast to the polymers constructed on the basis of acrylic acid, the polymers described according to the invention exhibit very good thickening properties even at an acidic pH.

The copolymers according to the invention are notable for their good thickening action, in particular in cosmetic and pharmaceutical preparations at concentrations of solid copolymer of from 0.1 to 5% by weight, preferably of from 2 to 0.5% by weight, particularly preferably of from 0.7 to 1% by weight, based on the finished composition. At room temperature in deionized water and at a pH of 6 to 7, viscosities of more than 60000 mPa.s are achieved.

The copolymers according to the invention exhibit only relatively slight changes in viscosity over a broad pH range, in particular in a range from pH 2.5 to 7. Furthermore, they retain their good solubility in water in the formulations and can be readily washed off from the skin. Their thickening and stabilizing properties are also effective in aqueous, alcoholic and/or glycol-containing solutions. They are UV stable and are stable over a wide temperature range from 0 to 50° C.

By varying the monomers acrylamidosulfonic acid salt and N-vinylcarboxamide, and the proportion of crosslinker, copolymers are obtained which can be used as thickeners both in oil-in-water emulsions, and in water-in-oil emulsions at a pH of from 7 to 2.5. Irrespective of whether the intention is to prepare lotions with a comparatively low viscosity, or creams and ointments with high viscosities, emulsions comprise an oil substance consisting essentially of emulsifier(s) and an oil phase in the amounts by weight of from 5 to 95%, preferably 25 to 85%, and water to make up 100% by weight. Suitable oil substances are vegetable, animal, mineral and synthetic oils, for example Guerbet alcohols having 6 to 18, preferably 8 to 10, carbon atoms, esters of linear $C_6$–$C_{13}$-fatty acids with linear $C_6$–$C_{20}$-fatty alcohols, esters of branched $C_6$–$C_{13}$-carboxylic acids with linear $C_6$–$C_{20}$-fatty alcohols, esters of linear $C_6$–$C_{18}$-fatty acids with branched alcohols, in particular 2-ethylhexanol, esters of linear and/or branched fatty acids with polyhydric alcohols (such as e.g. dimerdiol or trimertriol) and/or Guerbet alcohols, triglycerides based on $C_6$–$C_{10}$-fatty acids, vegetable oils, branched primary alcohols, substituted cyclohexanes, Guerbet carbonates, dialkyl ethers and/or aliphatic or aromatic hydrocarbons.

The emulsions may be in the form of skincare compositions, such as, for example, day creams, night creams, care creams, nourishing cream, body lotions, ointments and the like, and may comprise, as further auxiliaries and additives, coemulsifiers, superfatting agents, fats, waxes, stabilizers, biogenic active ingredients, glycerol, preservatives, pearlizing agents, dyes and fragrances.

Superfatting agents which may be used are substances such as, for example, polyethoxylated lanolin derivatives, lecithin derivatives, polyol fatty acid esters, monoglycerides and fatty acid alkanolamides, the latter also serving as foam stabilizers. Typical examples of fats are glycerides, and suitable waxes are, inter alia, beeswax, paraffin wax or microcrystalline waxes, optionally in combination with hydrophilic waxes, e.g. cetylstearyl alcohol.

Stabilizers which may be used are metal salts of fatty acids, such as e.g. magnesium stearate, aluminum stearate and/or zinc stearate. Biogenic active ingredients are understood as meaning, for example, plant extracts and vitamin complexes.

Suitable preservatives are, for example, phenoxyethanol, formaldehyde solution, parabens, pentanediol or sorbic acid.

Suitable pearlizing agents are, for example, glycol distearic esters, such as ethylene glycol distearate, but also fatty acid monoglycol esters. Dyes which may be used are the substances approved and suitable for cosmetic purposes, as listed, for example, in the publication "Kosmetische Farbemittel" [Cosmetic Colorants] from the Farbstoffkommission der Deutschen Forschungsgemeinschaft [Dyes Commission of the German Research Society], Verlag Chemie, Weinheim, 1984, pp. 81–106.

The total amount of auxiliaries and additives can be 1 to 10% by weight, preferably 2 to 5% by weight, based on the composition. The compositions can be prepared in a manner known per se, i.e. for example by hot, hot-hot/cold or PIT emulsification.

The examples below serve to illustrate the application possibilities of the thickeners according to the invention, without limiting them thereto. The percentages are percentages by weight in all cases.

| EXAMPLE 1 O/W cream | | |
|---|---|---|
| A | Hostacerin DGI | 2.00% |
|  | Mineral oil, low viscosity | 8.00% |
|  | Isopropyl palmitate | 4.00% |
|  | Eutanol G | 4.00% |
| B | Copolymer 1 | 1.20% |
| C | Hostapon KCG | 0.80% |
|  | Water | ad 100% |
|  | Preservative | q.s. |
| D | Fragrances | 0.40% |

Method of Preparation

I Stir B into A, then add C and stir well
II Stir D into I
III Homogenize

| EXAMPLE 2 O/W skin milk | | |
|---|---|---|
| A | Hostacerin DGMS | 2.00% |
|  | Mineral oil, high viscosity | 8.00% |
|  | Isopropyl palmitate | 5.00% |
|  | Cetiol 868 | 4.00% |
| B | Copolymer 2 | 0.50% |
| C | Hostapon KCG | 2.00% |
|  | Glycerol | 4.00% |
|  | Water | ad 100% |
|  | Preservative | q.s. |
| D | Fragrances | 0.30% |

Method of Preparation:

I Melt A to about 70° C.; add B
II Heat C to about 70° C.
III Stir II into I and stir until cool
IV Add D at about 35° C.
V Homogenize

| EXAMPLE 3 O/W skin milk | | |
|---|---|---|
| A | Hostacerin DCL | 2.00% |
|  | Isopropyl palmitate | 4.00% |
|  | Almond oil | 5.00% |
|  | Wheatgerm oil | 1.00% |
|  | Cetiol SN | 8.00% |
| B | Copolymer 1 | 0.60% |
| C | Water | ad 100% |
|  | Preservative | q.s. |
| D | Fragrances | 0.30% |

Method of Preparation:

I Mix A and B and stir into C
II Add D
III Homogenize

| EXAMPLE 4 O/W skin milk | | |
|---|---|---|
| A | Hostaphat CG 120 | 1.50% |
|  | Mineral oil, low viscosity | 5.00% |
|  | Miglyol 812 | 4.00% |
|  | Isopropyl palmitate | 6.00% |
|  | Soybean oil | 3.00% |
|  | Jojoba oil | 2.00% |
| B | Copolymer 1 | 0.80% |
| C | Hostapon KCG | 1.00% |
|  | Water | 100% |
|  | Glycerol | 3.00% |
|  | Soda (10% in water) | 1.20% |
|  | Preservative | q.s. |
| D | Fragrances | 0.30% |

Method of Preparation:

I Stir B into A, add C thereto and mix well
II Add D
III homogenize

| Commercial products | | |
|---|---|---|
| ®Hostacerin DGI | (Clariant GmbH) | Polyglyceryl-2 sesquiisostearate |
| ®Eutanol G | (Henkel KGaA) | Octyldodecanol |
| Copolymer 1 |  | Copolymer as in Example 1 |
| Copolymer 2 |  | Copolymer as in Example 2 |
| ®Hostapon KCG | (Clariant GmbH) | Sodium cocoyl glutamate |
| Hostacerin DGMS | (Clariant GmbH) | Polyglyceryl-2 stearate |
| ®Cetiol 868 | (Henkel KGaA) | Octyl stearate |
| Hostacerin DGL | (Clariant GmbH) | Polyglyceryl-2 PEG-10 laurate |
| ®Cetiol SN | (Henkel KGaA) | Cetearyl isononate |
| ®Hostaphat CG 120 | (Clariant GmbH) | Octyldecyl phosphate |
| ®Miglyol 812 | (Dynamit Nobel AG) | Capryl triglyceride |

What is claimed is:

1. A water-soluble or water-swellable crosslinked copolymer consisting essentially of a) 1 to 50% by weight of the repeating structural unit of the formula (1)

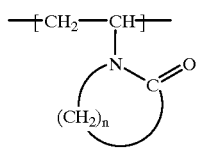 (1)

where n is an integer from 2 to 9,
b) 49.99 to 98.99% by weight of the repeating structural unit of the formula (3)

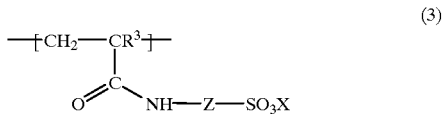 (3)

in which $R^3$ is hydrogen, methyl or ethyl, Z is $C_1$–$C_8$-alkylene, n is an integer from 2 to 9, and X is an alkali metal or alkaline earth metal ion, and
c) 0.01 to 8% by weight of crosslinking structures resulting from monomers having at least two olefinic double bonds selected from the group consisting of allyl acrylate, allyl methacrylate, allyl ethyl methacrylate, trimethylolpropane methacrylate, trimethylolpropane triacrylate, dipropylene glycol diallyl ether, polyglycol diallyl ether, triethylene glycol divinyl ether, hydroquinone diallyl ether, tetraallyloxyethane, tetraethylene glycol diacrylate, triallylamine, trimethylolpropane diallyl ether, methylene bisacrylamide, divinylbenzene, and mixtures thereof.

2. The copolymer as claimed in claim 1, consisting essentially of 2 to 30% by weight of the repeating structural unit of the formula 1, 69.5 to 97.5% by weight of the repeating structural unit of the formula 3 and 0.2 to 3% by weight of the crosslinking structures resulting from monomers having at least two olefinic double bonds.

3. The copolymer as claimed in claim 1, consisting essentially of 3 to 15% by weight of the repeating structural unit of the formula 1, 84.5 to 96.5% by weight of the repeating structural unit of the formula 3 and 0.5 to 2% by weight of the crosslinking structures resulting from monomers having at least two olefinic double bonds.

4. The copolymer as claimed in claim 1, comprising crosslinking structures resulting from allyl (meth)acrylate.

* * * * *